United States Patent [19]

Guillemin et al.

[11] 4,168,235

[45] Sep. 18, 1979

[54] SAMPLE SWEEPING AND INJECTION DEVICE FOR CHROMATOGRAPHY APPARATUS

[75] Inventors: Claude Guillemin, Paris; Christian Mayen, Creteil, both of France

[73] Assignee: Prolabo, Paris, France

[21] Appl. No.: 881,917

[22] Filed: Feb. 28, 1978

[30] Foreign Application Priority Data

Oct. 28, 1977 [FR] France .................... 77 33344

[51] Int. Cl.² ............................................. B01D 15/08
[52] U.S. Cl. ................................ 210/198 C; 210/291
[58] Field of Search ................. 210/31 C, 198 C, 291; 55/67, 386, 197

[56] References Cited

U.S. PATENT DOCUMENTS 3,884,802  5/1975  Spaans ........................... 210/198 C 4,035,168  7/1977  Jennings ........................... 55/67

Primary Examiner—John Adee
Attorney, Agent, or Firm—Burns, Doane, Swecker & Mathis

[57] ABSTRACT

In this device, for sweeping and injecting samples into the separation column of a chromatography apparatus, the separation column is secured to an opening connecting with a conduit which feeds a stream of carrier liquid to the device. The device subdivides a stream of carrier liquid into a primary stream and a secondary stream and feeds the primary stream over the entire cross section of the entrance to a separation column. Simultaneously feed of the secondary stream axially to the entrance of the separation column is performed while introducing the sample into the secondary stream. The device is usable particularly in liquid-phase chromatography.

11 Claims, 3 Drawing Figures

SAMPLE SWEEPING AND INJECTION DEVICE FOR CHROMATOGRAPHY APPARATUS

BACKGROUND OF THE INVENTION

This invention pertains to a sample sweeping and injection device for use in liquid-phase chromatography apparatus.

A liquid-phase chromatography apparatus comprises the following components, in the direction of flow:

(1) a reservoir for carrier liquid;

(2) a carrier liquid pumping system, to move said carrier liquid toward the separation column;

(3) a head for injecting the carrier liquid into the separation column;

(4) a system for injecting the sample to be analyzed;

(5) a separation column wherein the analysis takes place, that is, where the sample is separated into its various constituents; this column is filled with a packing or substrate;

(6) a detector of a type depending upon the nature of the molecules to be developed.

The functioning of the separation column of a liquid-phase chromatography apparatus may be affected by the geometry of the various components of the injection system-separation column assembly, more specifically by the presence of dead volumes and particularly by the precision with which the sample to be analyzed is injected at the head of the column, since the carrier liquid must percolate through the column at a slow, constant rate.

In high-performance liquid-phase chromatography, the samples to be analyzed are injected either by means of a syringe which pierces a partition or by means of a rotary valve or a slide valve. Volumes ranging from 1 microliter to more than 200 microliters can be injected, depending on the type of valve. These two means of injection both present drawbacks.

First, the conditions of injection with a syringe are difficult to reproduce from one analysis to the next and, second, the sample is often injected at a linear speed higher than the linear speed of the carrier liquid, thus giving rise to turbulence at the entrance to the separation column.

Valves can be used for quantitative analysis, because they yield a higher degree of reproducibility of injection conditions; nevertheless, their design causes the efficiency of separation to be reduced by one-half to as much as two-thirds of the number of theoretical bands attainable with ideal injections using syringes.

Thus, it is not unusual to obtain an efficiency of 8,000 theoretical bands using a syringe and a separation column 10 centimeters in length and 4 millimeters in inside diameter, while the same column may have an efficiency of no more than 3,000–4,000 theoretical bands when injected by means of a rotary or slide valve.

In an attempt to bring together the advantages of the syringe and valve modes of operation, it has been proposed to inject the sample by means of a loop injection valve centered on the end of the separation column and to feed the carrier liquid annularly all around the point of injection of the sample. To this end, a suitable injection chamber has been proposed, containing a sample injection tube and an annular chamber for distributing the carrier liquid around the injection tube at the head of the separation column. The carrier liquid is fed toward the injection chamber by means of a "T" coupling which distributes the carrier liquid to the annular distribution chamber through a capillary tube and to the sample loop injection valve through an all-or-nothing valve.

This mode of injection still presents drawbacks, however. In fact, before the sample is injected, all the carrier liquid drains toward the column through the capillary tube, with a great loss of head; at the moment the sample is injected, the greater part of the flow of the carrier liquid is directed toward the loop injection valve, causing the loss of head of the carrier liquid flow to change abruptly. This variation results in a variation in the flow of carrier liquid sweeping the separation column. This head loss variation consequently alters the rate of flow of the carrier liquid inside the separation column and consequently disturbs the analysis of the sample.

SUMMARY OF THE INVENTION

One objective of the present invention is to provide a sample injection device for a liquid-phase chromatography apparatus which avoids the drawbacks inherent in the syringe injection method and the valve injection method while retaining the respective advantages of each of these methods.

One object of the invention is to provide a device which simultaneously produces readily reproducible injection conditions and makes it possible to obtain chromatograms revealing a separation column efficiency similar to that obtained by means of an ideal syringe injection.

A further object of the invention is to provide an injection device which permits the sample to be injected at a linear speed equal to the linear speed of the carrier liquid.

Still another object of the invention is to provide a device which results in maintaining the carrier liquid flow conditions constant.

The present device has been devised for sweeping and injecting a sample into the separation column of a liquid-phase chromatography apparatus, it includes means to secure the separation column and an opening to feed a flow of carrier liquid into said device, said opening being connected with a conduit. Said device comprising:

(1) means for dividing a stream of said carrier liquid into a primary stream and a secondary stream;

(2) means to feed and distribute said primary stream over the entire cross section at the entrance of said separation column;

(3) means for simultaneously feeding said secondary stream axially at the entrance of said separation column; and (4) means to introduce said sample into said secondary stream.

BRIEF DESCRIPTION OF THE DRAWINGS

The invention will be more clearly understood by reference to the annexed drawings, which illustrate, by way of example only, a preferred embodiment of a device incorporating the present invention.

DESCRIPTION OF A PREFERRED EMBODIMENT

Figure 1:
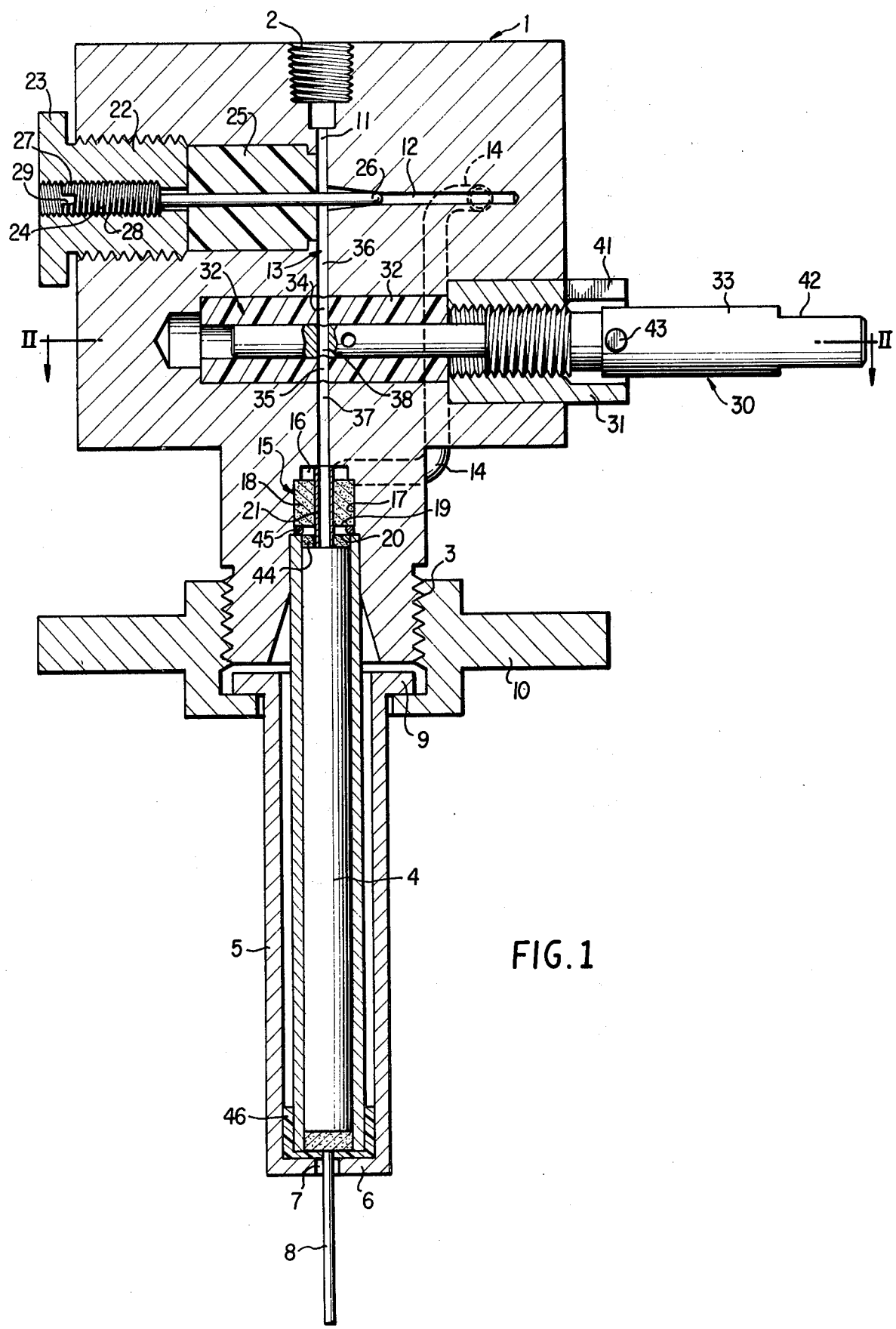
FIG. 1 is a cross section along a plane containing the centerline of the separation column of a device joined to a separation column.
Figure 2:
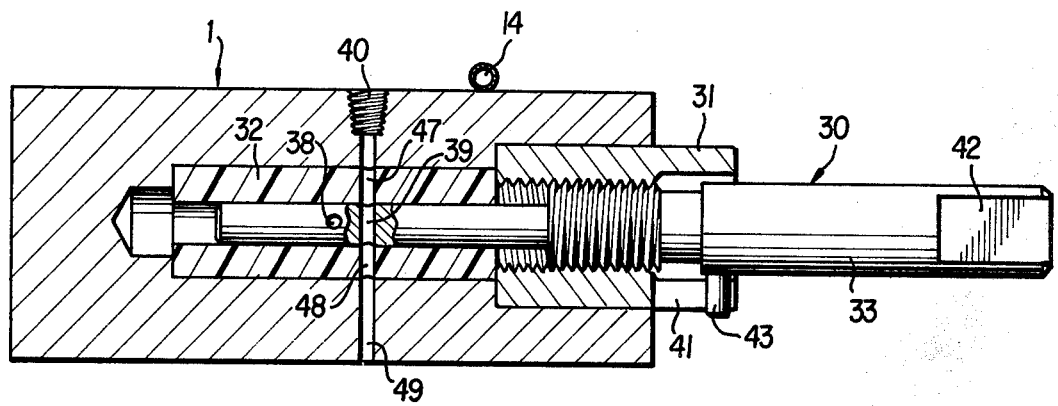
FIG. 2 is a cross-sectional view taken in the line II—II of FIG. 1.
Figure 3:
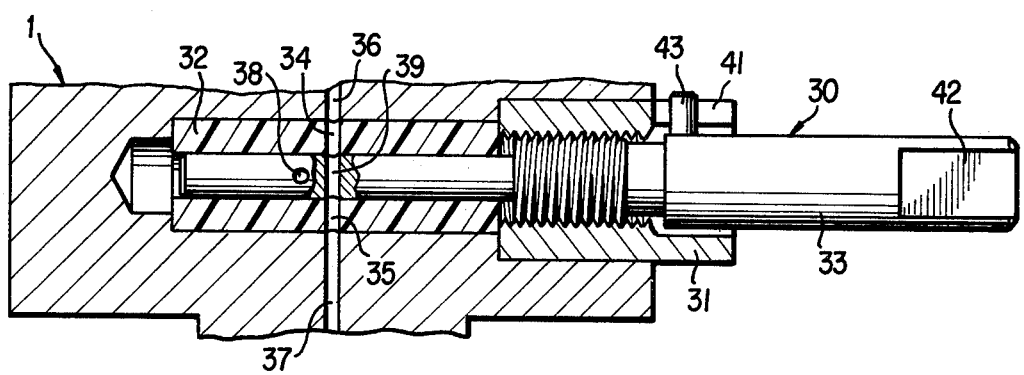
FIG. 3 is a cross section of a detail along a plane containing the centerline of the separation column of a device embodying the invention, as the sample is introduced.

One form of the device for sweeping and injecting a sample into the separation column of a liquid-phase chromatography apparatus is shown in FIGS. 1, 2 and 3.

This device consists of a block 1 having a supply inlet opening 2 for feeding a stream of carrier liquid and means 3 for securing the block 1 to the separation column 4.

The opening 2 may be threaded, for example, to permit easy connection with a suitable coupling.

The means 3 for securing the block 1 to the separation column 4 generally consist of a screw-threaded cylindrical portion.

The separation column may also be secured to the block 1 by using a suitable sleeve-type coupling.

Alternately, and preferably, the separation column 4 may be secured to the block 1, as is shown in FIG. 1, by a compressive stress applied substantially along the centerline of the column 4. Sealing gaskets 45 and 46 are positioned as shown and compressive stress is exerted on them by means of a substantially cylindrical column-holder tube 5, one end of which is closed by a wall 6 provided with a hole 7 through which passes an outlet tube 8 leading to the detector and the other end of which is provided with an external annular flange 9. A disc-shaped nut 10 engages the external annular flange 9 of the column-holder tube 5 and presses the same upwardly by means of the threaded cylindrical portion 3.

The sweeping and injection device also comprises means for dividing the stream of carrier liquid fed into the supply inlet 2, which communicates with the conduit 11, into a primary stream and a secondary stream, means to feed and distribute the primary stream over the entire cross section at the entrance 20 of the separation column 4, means to feed the secondary stream axially at the entrance 20 of the separation column 4, and means to introduce the sample to be analyzed into the secondary stream of carrier liquid.

The carrier liquid inlet 2 is in communication with the carrier liquid feed conduit 11.

As shown in FIGS. 1, 2 and 3, the dividing of the carrier liquid stream into a primary stream and a secondary stream is accomplished by directing some of the carrier liquid from feed conduit 11 into a primary conduit 12 and the remainder into a secondary conduit 13. In order to simplify the manufacture of the block 1, the primary conduit 12 is partially inside block 1 and partially outside block 1, the external portion preferably consisting of a small tube 14 whose extremities are joined to the portions of the primary conduit 12 which are inside the block 1 by such means as soldering.

The primary conduit 12 opens into a chamber 15 provided with means for distributing the primary stream of carrier liquid at the entrance 20 of the separation column 4. This chamber 15 consists of two zones, namely, a feed zone 16 and a distribution zone 17 provided with an insert 18. The insert 18 preferably consists of a cylinder of sintered or fritted metallic material. The feed zone 16 and distribution zone 17 are generally cylindrical. The entrance end 20 of the separation column 4 is held against the surface 19 of the insert 18 by the securing means 3.

The insert 18 contributes to the even distribution or diffusion of the primary stream of carrier liquid across the entrance 20 of the separation column 4, and also contributes to smoothing its flow by preventing the formation of turbulence eddies.

The means for feeding the secondary stream of carrier liquid to the entrance end 20 of the separation column 4 is the secondary conduit 13, which advantageously is of the capillary type. The secondary conduit 13 consists of the channels 36 and 37 inside the block 1, the holes 34 and 35 in member 32, the channel 38 and the hollow needle 21 which may be a tube soldered to the block 1. The holes 34 and 35 and the channel 38 are described below.

The hollow needle or tube 21 extends through the feed zone 16 and the distribution zone 17 and emerges at the end of the distribution zone 17 and extends through a porous wall 44 located at the entrance end 20 of the separation column 4 at its center, that is, axially with respect to the separation column 4. The length of the hollow needle or tube 21 is chosen so that said needle will terminate just at the interface between the porous wall 44 and the substrate of the separation column 4.

The means for dividing the flow of carrier liquid includes means to regulate the rate of flow of the primary stream. Such regulation means may consist, for example, of a needle valve 22. The needle valve 22 includes a hollow support 23, a needle element 24 and a sealing device 25. The hollow support 23 is substantially cylindrical and is provided with screw threads on its outer and inner surfaces so that it can be attached to the block 1 by screwing into a tapped hole. The conically tapered tip 26 of the needle element 24 extends into the extremity of the main conduit 12, which extremity is similarly tapered. The other end 27 of the needle element 24 is threaded at 28 whereby the needle is attached to the interior of the hollow support 23 and a notch 29 is provided for adjusting the valve by means of, say, a screwdriver, thus limiting the chances of accidentally altering its setting.

In the embodiment depicted in FIGS. 1, 2 and 3, the means for introducing the sample to be analyzed into the secondary stream of carrier liquid is a valve 30 of the piston-valve type.

The valve 30 consists of a valve support 31, a body 32 and a piston 33.

The valve support 31, generally cylindrical in shape, fits within a suitable cavity provided in the block 1 whose internal surface is provided at least in part with a screw thread. The portions of the support outside the body 1 has a cutout 41 bounded by two planes containing the axis of the cylinder and making an angle slightly larger than 90° with each other (to receive the pin 43 described below) and by a plane perpendicular to the axis of the cylinder.

The body 32 of the valve 30 is a hollow cylinder within a cylindrical chamber in the block 1; it contains two sets of two diametrically opposed holes longitudinally offset along the centerline of the hollow body and angularly offset at an angle of approximately 90°. The first such set of holes 34 and 35 are positioned so they communicate with the channels 36 and 37 of the secondary conduit. The second set of holes 47 and 48 communicate with channels 40 and 49 (see FIG. 2) which conduct the sample to be analyzed.

The body 32 is preferably formed of polytetrafluoroethylene, a material which not only permits the piston 33 to slide easily within the hollow body 32 but also provides a satisfactory tight seal by mere contact between the outer surface of the piston 33 and the inner surface of the body 32. In addition, polytetrafluoroethylene is highly inert to chemicals.

The piston 33 within the body 32 has the general shape of an elongated cylinder; along its length from the inside of the block 1 to the outside of said block it contains two zones, namely, the communication and sample injection zone on the inside of the block 1 and the control zone on the outside of the block 1.

The communication and sample injection zone is defined by the channel 38 and a compartment 39 for the sample to be analyzed. The channel 38 and the compartment 39 are substantially diametral and extend completely across the piston 33. They are located some distance apart along the longitudinal axis of the piston 33 and angularly offset by an angle of approximately 90°. When the piston 33 is in an axial and rotational position such as that shown in FIGS. 1 and 2, the channel 38 provides a connection between the holes 34 and 35 of the secondary conduit 13, while the compartment 39 is then simultaneously in communication with the channels 40 and 49 which feed the sample to be analyzed. The channel 40 is preferably threaded near the outside of the block 1 in order to permit a coupling to be easily attached to it. In another axial and rotational position of the piston 33, such as that depicted in FIG. 3, the connection between the holes 34 and 35 is established by the compartment 39 and the channel 38 is closed.

The movement of piston 33 from the position depicted in FIGS. 1 and 2 to the position depicted in FIG. 3 is a translation along the piston axis for a distance equal to the longitudinal separation between the channel 38 and the compartment 39 and a simultaneous rotation around said axis through an angle equal to the angular offset between the channel 38 and the compartment 39.

The control zone has means for securing the piston 33 to the support 31 and control means.

The means for securing the piston 33 to the support 31 is a threaded region which screws into the tapped inner surface of the support 31.

The control means consist in part of a flat 42 at the end of the piston 33, which flat permits this end to be gripped easily when the piston 33 is operated, and in part of the pin 43 which moves within the cutout 41 of the support 31 and stops against one of the two planes containing the centerline of the piston 33 at each position of the piston 33, namely the positions where the channel 38 or the compartment 39 are in connection with the secondary conduit 13.

The functioning of the sample sweeping and injection device is described hereafter.

After the carrier liquid inlet aperture 2 is connected to a carrier liquid source (not shown), the separation column 4 is installed in place and held by a substantially axial compressive stress such as has been described above; the hollow needle or tube 21 extends through the porous wall 44 and terminates just at the interface between the porous wall and the substrate. The channel 40 is then connected to a source of the sample to be analyzed (not shown). The device for sweeping and injecting the sample into the separation column of a chromatography apparatus is then ready for the analysis and the flow of carrier liquid is started.

With the piston 33 in the position depicted in FIGS. 1 and 2, the needle valve is adjusted to regulate the rate of flow of the primary stream according to the conditions of the analysis to be performed. The primary stream then flows through the primary conduit 12 and is uniformly distributed on the substrate, concentrically around the hollow needle 21, over the entire cross section of the separation column 4.

The secondary stream flows through the capillary secondary conduit 13, that is, through channel 36, hole 34, channel 38, hole 35, channel 37 and the hollow needle 21, and is fed axially at the entrance end 20 of the separation column, immediately below the porous wall 44. At the same time, the sample to be analyzed has filled the compartment 39.

To inject the sample now contained in the compartment 39, the piston 33 is made to move by combined translation and rotation (guided by the pin 43 which moves within the cutout 41) in such a fashion as to bring the compartment 39 into communication with the holes 34 and 35, in place of the channel 38, as depicted in FIG. 3. The secondary flow which flows through the capillary conduit 13 then sweeps the sample contained in the compartment 39 and entrains it axially into the separation column 4.

It is understood that the invention is not limited solely to the embodiment specifically described, and that variations or improvements can be made without thereby exceeding the scope of the invention.

For example, the piston valve described above may be replaced by a slide valve. The slide of such a valve may be provided with a channel analogous to the channel 38 and a compartment analogous to the compartment 39 of the piston valve. The channel and the compartment may be substantially cylindrical, have parallel axes and traverse the slide at a small longitudinal distance from each other. Thus, at one position of the slide, the channel connects with the secondary flow conduit and the compartment connects with the feed channel of the sample to be analyzed. By moving the slide by translation, the compartment containing the sample could be brought into communications with the secondary conduit and the secondary flow would then sweep the sample.

The piston valve may also be replaced with a rotary valve wherein a rotatable disc could be provided with a channel and a compartment. The channel and the compartment may be substantially cylindrical, have parallel axes, extend completely through the disc, and be located at equal distances from the axis of rotation of the disc and angularly offset. Rotation of the disc would bring the compartment into communication with the secondary conduit and the secondary flow would sweep the sample.

Also without going beyond the scope of the invention, the piston valve may be replaced by a barrel valve. Such a valve is similar to a rotary valve, the valve could contain several compartments, so that repeated injections or multiple injections could be carried out.

The scope of the invention is also not exceeded if automatic control means, such as a servomotor, for example, are added to the means which introduce the sample into the secondary flow.

The device for sweeping and injecting the sample into the separation column of a chromatography apparatus which is the object of the invention exhibits numerous advantages.

Such a device makes it possible to achieve injection conditions which are reproducible from one analysis to the next, since the speed of injection of the sample is identical from one analysis to the next and equals the speed of the secondary stream of carrier liquid. Moreover, the flow conditions of the carrier liquid inside the separation column do not change at the moment when the sample is injected. In particular, no change takes place in the rate of flow within the separation column, since the separation column is traversed by the carrier liquid at the same speed both before the sample is injected and while it is being injected.

Furthermore, such a device is particularly advantageous for use upstream of a short separation column. In effect, when short separation columns are used, the loss of head of the carrier liquid upstream of the separation column is significant in relation to the loss of head induced within the separation column itself. It is therefore important that the head loss upstream of the separation column should not vary during the course of the analysis, and the device which is the object of our invention does not entail any variation in the head loss upstream of the separation column.

The device according to the invention also exhibits the advantage of effecting the sample injection under conditions similar to the ideal conditions of injection with a syringe, since the sample to be analyzed is injected into the separation column immediately below the porous wall by a capillary conduit, which makes it possible to improve the performance of separation columns thanks to the perfectly centered injection of the sample at a constant level at the head of the column. In addition, since the main flow of carrier liquid is distributed concentrically around the sample, it prevents radial diffusion of the sample.

Another advantage of the device according to the invention is the increase in the efficiency of the separation column. Thus, all things being otherwise equal, an efficiency of 7,500 theoretical bands has been measured on the naphthalene peak of a mixture of toluene, naphthalene and anthracene when using a sweeping and injection device embodying this invention, while an efficiency of 7,000 theoretical bands is obtained when a syringe is used for injecting the sample.

While the invention has been described in terms of various preferred embodiments, the skilled artisan will appreciate that various modifications, substitutions, omissions, and changes may be made without departing from the spirit therof. Accordingly, it is intended that the scope of the present invention be limited solely by the scope of the following claims.

What is claimed is:

1. In a device for sweeping and injecting samples into a separation column of a liquid-phase chromatography apparatus, having means for securing the same to the inlet of a separation column, a supply inlet for a stream of carrier liquid and means for directing said stream to said separation column:
    dividing means in said device for dividing said stream into primary and secondary streams;
    distributing means for directing said primary stream to said separation column and distributing said primary stream over the entire inlet area of said column;
    means directing said secondary stream axially into the center of said separation column inlet; and
    means for introducing a sample into said secondary stream.

2. A device as defined in claim 1 wherein said dividing means include primary and secondary conduits communicating with said supply inlet.

3. A device as defined in claim 1 wherein said dividing means include control means to regulate the rate of flow in said primary stream.

4. A device as defined in claim 3 wherein said control means comprises a needle valve.

5. A device as defined in claim 1 wherein said distributing means includes means defining a feed zone and a distribution zone.

6. A device as defined in claim 5 wherein said distribution zone comprises a body for diffusing said liquid.

7. A device as defined in claim 6 wherein said body comprises a porous body of sintered metallic material.

8. A device as defined in claim 1 wherein said means for directing said secondary stream comprises a capillary conduit including a hollow needle.

9. A device as defined in claim 1 wherein said last-named means comprises a piston valve.

10. A device as defined in claim 1 wherein said last-named means comprises a rotary valve.

11. A device as defined in claim 1 wherein said last-named means comprises a barrel valve.

* * * * *